United States Patent [19]

Johnson et al.

[11] 4,054,538

[45] Oct. 18, 1977

[54] π ALLYL CHROMIUM COMPLEX CATALYST AND PROCESS FOR PREPARING SAME

[75] Inventors: Robert N. Johnson, Basking Ridge; Frederick J. Karol, Somerset, both of N.J.

[73] Assignee: Union Carbide Corporation, New York, N.Y.

[21] Appl. No.: 385,304

[22] Filed: Aug. 3, 1973

Related U.S. Application Data

[60] Division of Ser. No. 193,144, Oct. 27, 1971, Pat. No. 3,836,595, which is a continuation-in-part of Ser. No. 878,566, Nov. 20, 1969, abandoned, which is a continuation-in-part of Ser. No. 784,478, Dec. 17, 1968, abandoned.

[51] Int. Cl.$^2$ .................................................. C08F 4/78
[52] U.S. Cl. .................................. 252/428; 252/430; 252/431 R; 526/130; 526/170
[58] Field of Search .................. 252/430, 431 R, 428; 260/683.15 D, 94 D

[56] References Cited

U.S. PATENT DOCUMENTS

| 3,157,712 | 1/1964 | Walker et al. ............. 260/683.15 D |
| 3,379,706 | 4/1968 | Wilke ......................... 252/431 R |
| 3,493,554 | 2/1970 | Rekers ........................ 252/431 R |
| 3,535,297 | 10/1970 | Carrick et al. .................. 252/467 |
| 3,620,981 | 11/1971 | Magoon et al. .............. 252/431 R |
| 3,627,700 | 12/1971 | Zuech ....................... 260/683.15 D |
| 3,709,853 | 1/1973 | Karapinka ................. 260/683.15 D |

*Primary Examiner*—Patrick P. Garvin
*Attorney, Agent, or Firm*—James J. O'Connell

[57] ABSTRACT

Ethylene polymerization catalyst which is π allyl chromium compound in the chromium [II] valence state and supported on silica or silica-alumina, and a process for making such catalyst.

8 Claims, No Drawings

π ALLYL CHROMIUM COMPLEX CATALYST AND PROCESS FOR PREPARING SAME

CROSS REFERENCES TO RELATED PATENT APPLICATIONS

This patent application is a division of application Ser. No. 193,144 filed Oct. 27, 1971, now U.S. Pat. No. 3,836,595 which was a continuation-in-part of application Ser. No. 878,566 filed Nov. 20, 1969, which was a continuation-in-part of application Ser. No. 784,478 filed Dec. 17, 1968, said applications Ser. No. 878,566 and Ser. No. 784,478 both being abandoned.

BACKGROUND OF THE INVENTION

This invention relates to an improved catalyst system for the polymerization of ethylene to form ethylene homopolymers and interpolymers and ethylene and other α-olefins and/or diolefins.

U.S. Pat. No. 3,379,706 discloses that certain π allyl metal compounds have activity as polymerization, including oligomerization, catalysts. With respect to the polymerization of ethylene, it is disclosed, for example, that tris π-allyl chromium (π allyl chromium [III]) will polymerize ethylene to form linear polyethylenes having infra-red spectra identical with the spectra of the so-called Ziegler polyethylenes at a level of productivity, however, in the order of only 5-36 grams of polymer per gram of chromium per hour.

SUMMARY OF THE INVENTION

It has now been found that in the catalytic polymerization of ethylene using an allyl chromium compound as the catalyst, productivity can be increased by as much as 1 million percent by using, as the catalyst a π allyl chromium complex wherein at least part of the chromium is in the chromium [II] valence state and the complex is supported or deposited on an inorganic oxide having a high surface area.

Based on this discovery, there is also provided an improved process for forming a π allyl chromium compound catalyst which has a high level of productivity by either reducing at least a portion of a π allyl chromium [III] compound to the chromium [II] valence state or by directly preparing a π allyl chromium [II] compound, and then depositing or absorbing the reduced or directly prepared π allyl chromium compound onto an inorganic oxide having a high surface area.

DESCRIPTION OF THE PREFERRED EMBODIMENT

According to the present invention, a π allyl chromium compound having at least a portion of the chromium in the [II] valence state and supported on an inorganic oxide having a high surface area provides an ethylene polymerization catalyst having an unusual high level of productivity. p The π allyl compound having at least a portion of the chromium in the [II] valence state may be prepared in various ways. In one procedure a π allyl chromium [II] compound may be prepared directly from divalent chromium, as disclosed for example by Kurras and Klimsch, Monatsber, Deut, Akad, Wiss, Berlin 6, 736 (1964), which disclosure is incorporated herein by reference. The π allyl compounds used in the present invention may also be prepared by first preparing a π allyl chromium [III] compound or complex and then reducing at least a portion of the chromium [III] compound to the [II] valence state.

The π allyl chromium [III] complexes used in the preparation of the catalysts of this invention are generally obtained by reacting chromium trichloride and allyl magnesium bromide at temperatures below about −17° C. A convenient method for their preparation is also set forth in Kurras and Klimsch, supra which disclosure is also incorporated herein by reference. The allyl chromium [III] complexes so formed are stable in solution at temperatures below about −17° C., but will transform to complexes containing chromium in a lower valence state at higher temperatures.

In addition to being reduced by the use of elevated temperatures, it is believed that the π allyl chromium [III] compounds may also be reduced sufficiently to the chromium [II] valence state for the purposes of the present invention by the use of other physical means such as by the use of high energy electrons, electric discharge, X-rays and γ rays.

In giving consideration to the allyl chromium complexes as ethylene polymerization catalysts it was decided to determine the effect of using an inert inorganic oxide support on catalytic activity. When a sample from a fairly fresh stock solution of π allyl chromium [III] was adsorbed onto a high surface area silica gel support which had been previously activated at 580° C., and the supported compound was used as an ethylene polymerization catalyst, essentially only a dimerization of the ethylene to the butenes and some higher olefins occurred at normal ethylene polymerization temperatures, even though the supported allyl chromium [III] was exposed to polymerization temperatures above 70° C. This is somewhat significant because a dimerization of ethylene has only been previously occasioned by the use of aluminum alkyls as catalysts and not with organic chromium compound catalysts.

The stock solution was then allowed to warm to room temperature and remain at room temperature for about 10 minutes and a precipitate was observed to form suggesting the reduction of chromium to a lower valence state. A sample of this solution was then adsorbed onto a high surface area silica gel support which had been previously activated at 350° C. and quite unexpectedly the supported allyl chromium compound became highly active for the polymerization of ethylene to high molecular weight, high density polymers which gave infra-red spectra quite different from the infra-red spectra of the so called Ziegler polyethylenes.

Even more surprising was the significant increase in the level of productivity of the supported catalysts. In comparison to the highest level of productivity, of 36 grams of polymer per gram of chromium per hour, reported by Wilke in U.S. Pat. No. 3,379,706, it was possible to achieve a producitivity of about 400,000 grams of polymer per gram of chromium per hour with the supported catalysts of the present invention. This is an improvement in the order of over 1 million percent.

While not wishing to be bound by any theory, it is believed that, when reduced, the π allyl chromium [III] is reduced in solution to an active species which must be present where absorption onto the inorganic oxide occurs. This active species is believed to be π allyl chromium [II] which is the first complex formed in the reduction of π allyl chromium [III] and which is further believed to exist as a dimer consisting of two chromium atoms and four allyl groups. The solution, moreover, appeared to be in some transistory state wherein the π allyl chromium [II] complex exists with π allyl chromium [III] in some dynamic equilibration with complexes wherein chromium is in a still lower valence state as is presumably caused by a further reduction of π allyl chromium [II]. This was indicated by the observation that once reduction started, and the solution was repeatedly warmed to about 5° C. for short periods of time to effect syringe removal of samples for supported catalyst preparation, the solution, over a 2 week period, appeared to reach a state which yielded a supported catalyst of peak productivity followed by a period in which supported catalysts of progressively declining productivity were obtained.

What is equally significant is that mere adsorption of a allyl chromium [III] complex onto a support is not the route to a high productivity ethylene polymerization catalyst for it has been observed that subjecting an adsorbed π allyl chromium [III] compound to the elevated temperatures usually associated with low pressure ethylene polymerizations would not yield high molecular weight polymers. Rather, the formation of an active catalyst from a π allyl chromium [III] compound having a high level of productivity requires the step of reduction prior or subsequent to deposition of the compound onto the support.

As suggested above, conditioning a π allyl chromium [III] compound for deposition to form an active catalyst requires only a simple heating to room temperature for a period of from about 1 to about 30 minutes. Reduction to the active form is generally signaled by the formation of an inactive by-product precipitate. Once this occurs the solution may be used in its entirety or returned to a reduced temperature of the order of about −78° C. for preservation. In this instance where the solution is consumed on a batch-wise basis using techniques which require temperature elevation to avoid moisture condensation, it has been observed that aging continues and finally results in an eventual loss of activity after about 15 or so recycles to temperatures above about −17° C., the currently accepted minimum reduction temperature for π allyl chromium [III], and presumably the lower valence complexes as well.

While conversion of π allyl chromium [III] to the allyl chromium [II] complex will occur at room temperature over a period of time, conversion can also be achieved at other temperatures of from about −17° C. up to about 80° C., as long as adequate time is provided for the reduction to occur. Again it is pointed out that the reduction may be detected by observing the formation of the precipitate.

To prepare the thoroughly active catalyst of this invention the reduced π allyl chromium [III] complex or the directly prepared π allyl chromium [II] complex is contacted with, and supported on or adsorbed by, a substantially anhydrous inorganic oxide. Among the various inorganic oxides which may be used to form the supported catalyst are silica, alumina, thoria, zirconia, and comparable oxides, and mixtures thereof, particularly silica-alumina mixtures, all of which supports are chemically inert with respect to reducing the activity of the π allyl chromium complex. To be effective, these supports must have a high surface area to adsorb a sufficient quantity of the π allyl chromium complex and provide sufficient contact between the catalyst and the monomer. As a general rule, inorganic oxides having a surface area in the range from about 50 to about 1000 square meters per gram should be employed as the catalyst support. The particle size of these supports is not particularly critical, provided however, that the support has a high surface area.

To prepare a suitable catalyst the support should be completely dried before it is brought into contact with the organochromium compound. This is normally done by simply heating or pre-drying the catalyst support with an inert gas prior to use.

In this respect, the temperature of drying can have an effect on both the relative level of productivity of the catalyst and on the molecular weight distribution and the melt index of the polymer produced.

Drying or activation of the support can be accomplished at nearly any temperature up to about its sintering temperature for a period of time at least sufficient to remove the absorbed water while avoiding heating which will remove all of the chemically bound water. Passing an inert gas stream through the support during the drying desirably aids in the displacement of the absorbed water. Temperatures of from about 200° to 900° C. for a short period of about 6 hours or so should be sufficient if a well dried inert gas is used and the temperature is not permitted to get so high as to remove completely the chemically bound hydroxyl groups on the surface of the support.

Any grade of support can be used herein but microspheroidal intermediate density (MSID) silica having a surface area of 258 square meters per gram and a pore diameter of about 200 A, and intermediate density (ID) silica having the same area but a pore diameter of 164 A are preferred. Other grades such as the G-968 silica and G-966 silica-alumina, as so designated by W. R. Grace and Co., having surface areas of 700 and 500 square meters per gram, respectively, and pore diameters of 50–70 A, are also quite satisfactory. Variations in melt index control and in the level of polymer productivity can be expected between different grades of supports, and also as a result of the use of different activation temperatures.

After the supported π allyl chromium catalyst has been formed, the polymerization reaction is conducted by contacting ethylene, alone, or with other olefins being copolymerized therewith, substantially in the absence of moisture and of air, with a catalytic amount of the catalyst at a temperature and at a pressure sufficient to initiate the polymerization reaction. If desired, an inert organic solvent may be used as a diluent and to facilitate materials handling.

The polymerization reaction is carried out at temperatures of from about 30° C. or less up to about 200° C. or more, depending to a great extent on the operating pressure, the pressure of olefin monomers other than ethylene that may be present, the pressure of modifying gases that may be present in the system, as well as on the particular catalyst and its concentration. Naturally, the selected operating temperature is also dependent upon the desired polymer melt index since such temperature is definitely a factor in adjusting the molecular weight of the polymer. Preferably, the temperature is from about 30° to about 100° C. in the conventional slurry or "particle forming" technique and from 100° to 200° C. in "solution forming." Low density ethylene polymers are made using the "solution forming" process. Low density ethylene homopolymers can also be prepared using the "particle forming" process if the support activation temperature is 580° C or 420° C if ethylene copolymers are to be prepared. The control of temperature in this process is desirable, as hereinafter more fully described, in providing various effects upon the molecular weight of the polymers as well as in controlling the phase in which they are made. As with most catalyst systems, the use of higher temperatures results in the production of the lower weight average molecular weight polymers, and consequently of polymers having a higher melt index.

The pressure can be any pressure sufficient to initiate the polymerization of the monomer to high molecular weight polymer. The polymerization can be carried out therefore, from subatmospheric pressure, using an inert gas as a diluent, to superatmospheric pressure of up to about 1,000,000 p.s.i.g. or more, but the preferred pressure is from atmospheric up to about 1000 p.s.i.g. As a general rule, a pressure of 20 to 800 p.s.i.g. is preferred. However, as can be seen from the discussion and the appended examples, a wide latitude of pressures can be employed to secure the high molecular weight polymers.

The selection of an inert organic solvent medium to be employed in the process of this invention is not narrowly critical, but the solvent should be inert to the supported $\pi$ allyl chromium catalyst and the olefin polymer produced, and be stable at the reaction temperature used. It is not necessary, however, that the inert organic solvent medium serve also as a solvent for the polymer produced. Among the inert organic solvents applicable for such purpose may be mentioned saturated aliphatic hydrocarbons, such as hexane, heptane, pentane, isooctane, purified kerosene and the like, saturated cycloaliphatic hydrocarbons, such as cyclohexane, cyclopentane, dimethylcyclopentane and methylcyclohexane and the like, aromatic hydrocarbons such as benzene, toluene, xylene, and the like and chlorinated hydrocarbons, such as chlorobenzene, tetrachloroethylene, orthodichlorobenzene and the like. Particularly preferred solvent media are cyclohexane, pentane, hexane and heptane.

When it is desired to conduct the polymerization to a high solids level as hereinbefore set forth, it is of course desirable that the solvent be liquid at the reaction temperature. For example, operating at a temperature less than the solution temperature of the polymer in the solvent, the process can be essentially a slurry or suspension polymerization process in which the polymer actually precipitates out of the liquid reaction medium and in which the catalyst is suspended in a finely divided form.

The slurry system is of course dependent upon the particular solvent employed in the polymerization and the solvent's solution temperature for the polymer prepared. Consequently, in the "particle form" embodiment, it is most desirable to operate at a temperature which is lower than the normal solution temperature of the polymer in the selected solvent. As for example, polyethylene prepared herein has a solution temperature in cyclohexane of about 90° C., whereas in pentane its solution temperature is about 110° C. It is characteristic of this "particle form" polymerization system that a high polymer solids content is possible even at low temperatures provided agitation is present to enable adequate mixing of the monomer with the polymerizing mass. It appears that while polymerization rate may be slightly slower at the lower temperatures, the monomer is more soluble in the solvent medium thus counteracting any tendency to low polymerization rates and/or low yields of polymer.

It is also characteristic that the monomer appears to have substantial solubility characteristics even in the solids portion of the slurry so that as long as agitation is provided and polymerization temperatures maintained, a broad range of size of solid particles in the slurry can be provided. Experience has shown that the slurry technique can produce a better than fifty percent solids system, provided sufficient fluidizing conditions and agitation are maintained. It is particularly preferable to operate the slurry process in the range of 30–40 weight percent of polymer solids.

Recovery of the polymer from the solvent medium is simplified to a simple filtration and drying operation and no efforts need be expended in polymer clean up and catalyst separation or purification. The residual concentration of catalyst in the polymer is so small, that generally less than two to three parts of chromium per million parts of polymer can be achieved, and at such levels they are innocuous and unnoticed in the polymer. Expeditiously, they can be left in the polymer.

Operating at temperatures higher than the solution temperature of the polymer in the selected solvent medium also can produce a high polymer solids content in solution. The temperature employed in this embodiment of this invention must be sufficiently high so as to enable the solvent being used to dissolve at least 25–30 percent by weight of the polymer. On the other hand, the temperature must be sufficiently low to avoid thermal destruction of the formed polymer and the catalyst. In general, for the various solvents and the $\pi$ allyl chromium catalyst used, temperatures within the range of about 100° to about 200° C., and preferably about 120° to about 170° C., have been found to be generally optimum for the practice of such solution polymerization. However, the particular polymer being produced also has a significant effect on the optimum temperature. For example, ethylene-propylene copolymers produced by this process are soluble in many of these organic solvents at low temperatures and hence the use of such temperatures is permissible in this invention even though such temperatures may not be desired for the optimum production of ethylene homopolymers or other copolymers.

Solvents constitute one of the most significant and vexing sources of catalyst poisoning. Moreover, in prior solution polymerization processes employing transition metal-containing catalysts, the use of large quantities of solvent, i.e., a solvent-to-polymer weight ratio of the order of 20:1, was believed necessary. Such large proportions of solvent necessarily greatly increased the catalyst poisoning problem. In the present process, however, the proportion of solvent to polymer can be as low as 1:1 or even less, thereby maintaining a very high level of catalyst productivity and efficiency for the system.

When the solvent serves as the principal reaction medium, it is of course desirable to maintain the solvent medium substantially anhydrous and free of any possible catalyst poisons, by redistilling or otherwise purifying the solvent before its use in this process. Treatment with an absorbent such as high surface area silicas, aluminas, molecular sieves and like materials are beneficial in removing trace amounts of contaminants that may reduce the polymerization rate or poison the catalyst during the reaction.

However, it is also possible to operate the polymerization reaction without an added solvent reaction medium, if desired. For example, the liquid monomer itself can be the reaction medium, either with the normally commercially liquid monomers as in making ethylene-propylene copolymers using liquefied propylene and other similar commercially liquefied monomers, or by operating under sufficient pressure that a normally gaseous monomer is liquefied.

The fact that the polymerization rate remains high even with the high viscosities encountered at the high solids level, is unexpected. It is particularly surprising and unexpected that the reaction rate remains high when normally gaseous monomers such as ethylene and propylene are employed. We have found, however, that high polymerization rates are maintained even when using these gaseous monomers at pressures under 100 p.s.i.g. when the reaction solution is agitated by means of a high velocity, high shear stirrer, particularly one driven at speeds in excess of 2000 r.p.m. and designed to impart considerable shearing action on the solution.

Another particularly important advantage afforded by the present process is that the high solids content polymer solution, upon completion of the polymerization reaction, is, without any further treatment, suitable for polymer isolation, by milling techniques, such as those described in U.S. Pat. No. 2,434,707 to W. A. Marshall, which patent is incorporated herein by reference.

Still another advantage of the present process is provided by maintaining the catalyst and the polymer, as formed, in homogeneous solution in the solvent medium. By avoiding the formation of a polymer suspension, the reaction mass behaves surprisingly as a viscous fluid which can be pumped and handled by any of the standard techniques for handling fluids.

Still another advantage of having the polymer soluble in the diluent is that high reaction temperatures can be employed. This is advantageous because the high temperatures reduce the viscosity of the solution. They also cause the polymerization to proceed faster and allow for a more efficient removal of the heat of reaction because of the large temperature differential between the reactor and the cooling water, and also permit control of the polymer molecular weight since high reaction temperatures generally cause the formation of lower molecular weight polymers.

The separation of polymer from the solvent medium is not limited in this invention to the use of a high shear mill, although a Marshall mill has been found to be well suited for use herein and is preferred. However, it is also possible to employ filtration techniques to recover the polymer, or to concentrate the polymer/solvent mass by flash evaporation, or other means of solvent removal followed by high shear milling. A number of other suitable high shear mills are commercially available and because of the low solvent content of the solution to be treated, other devices such as vented extruders, calendaring roll mills, planetary rotor mills such as the one described in U.S. Pat. No. 3,075,747 to W. L Calvert, Banbury mills, and the like, can also be successfully employed to accomplish isolation of the polymer product. By the term "high shear mill" as used hereinafter is meant a mill comprising parallel rolls having intermeshing threads, and the term "high shear conditions" and "conditions of high shear" are those conditions achieved on a high shear mill or by adequately powered high speed mixers for viscous materials.

It should be understood that the high solids systems can be employed with the catalyst suspended in the solvent, provided that the necessary conditions of agitation, pressure, temperature, and the like are maintained so as to provide contact of the monomer with the catalyst, and that the pressure and temperature are such as to initiate the polymerization of that monomer to the desired polymer.

It should also be understood that the invention herein contemplated, includes the techniques of fluidizing the solid catalyst bed in a gaseous system by fluxing the bed with a gaseous olefin feed thereby eliminating the use of liquid solvents and the attendant problems of solvent separation and catalyst poisons as hereinbefore mentioned.

The amount of concentration of supported $\pi$ allyl chromium catalyst employed in this invention is not critical and generally only affects the rate and yield of polymer secured. It can be varied from about 1 to 100,000 preferably from 1 to 25,000 parts per million of catalyst, based on the weight of olefin charged. Preferably, and for greatest economy of operation, the catalyst concentration is maintained from about 5 to 100 parts per million. Obviously, the lower the impurity level in the reaction system, the lower the catalyst concentration that can be used. Experience has shown that yields greater than 400,000 grams of polymer per gram of chromium may be obtained. This is significant since Wilke in U.S. Pat. No. 3,379,706 reports yields only as high as 36 grams of polymer per gram of chromium, and, as will be shown, a supported catalyst made by starting with a mixture of allyl chromium II and III deposited on a silica gel activated above 400° C. and preferably $\geq 580°$ C., will essentially cause oligomerization of ethylene to butenes and some higher olefins.

Among the α-olefins which can be polymerized with ethylene in accordance with the invention are those containing from 3 to about 10 carbon atoms. Illustrative thereof but not limiting in this regard are propylene, butene-1, pentene-1, 3-methylbutene-1, hexene-1, 4-methylpentene-1, 3-ethylbutene-1, heptene-1, octene-1, decene-1, 4,4-dimethylpentene-1, 4,4-diethylhexene-1, 3,4-dimethylhexene-1, 4-butyl-1-octene, 5-ethyl-1-decene, 3,3-dimethylbutene-1, and the like. Such compounds can be polymerized in combination with a major amount of ethylene to yield normally solid, high molecular weight interpolymers of ethylene and one or more of such α-olefins. Ethylene (alone or with minor amounts of other α-olefins) may also be polymerized with diolefins to yield normally solid, cross-linkable interpolymers. Among the diolefins which may be used are butadiene, 1,5-hexadiene, dicyclopentadiene, ethylidene norbornene, and the like. Homopolymers of ethylene are the particularly preferred polymers. The particularly preferred interpolymers are ethylene-propylene or ethylene-butene interpolymers, having up to about 20 weight percent of the interpolymerized propylene or butene.

Care should be taken during the polymerization to avoid the introduction of moisture and air (oxygen) which are catalyst poisons.

Ethylene polymers prepared with the catalyst of this invention may be generally classed as high (0.94–0.97) or low (0.91–0.92) density, high molecular weight polymers. They differ, however, in infra-red spectra from the so-called Ziegler and Phillips polymers and represent a new family of polymers whose formation is unique as to the nature of the growing polymer chains. The growing chains may be of the usual linear type where the chromium is always bonded to a primary $CH_2$ carbon atom or of branched type where the chromium becomes attached to a secondary carbon by an isomerization reaction that occurs concomitantly with the polymerization.

THE EXAMPLES

In the examples certain properties were determined using the following standards.

| Melt Index (MI) | ASTM D-1238-62T |
| Melt Flow (MF) | ASTM D-1238-62T at 440 psi and 190° C. |
| Density | ASTM D-1505 |

EXAMPLE 1

Employing the directions of Kurras and Klimsch, Monatsber, Deut. Akad. Wiss Berlin 6,736 (1964) a supply of allyl chromium [III] complex was prepared by reacting allyl magnesium bromide with chromium trichloride at −20° C. under a slight argon pressure. Excess allyl magnesium bromide was destroyed by then purging the solution with dry, oxygen free, carbon dioxide. The inorganic magnesium salts were removed by filtration at −20° C., and the ether distilled off in a vacuum at −20° C. and replaced with dry hexane. The resultant solution which contained allyl chromium in a concentration of about 0.5 Molar was immediately cooled to −78° C. for storage.

CONTROL A

The stock solution prepared in Example 1 was allowed to warm to about 5° C. and a 0.5 ml sample was withdrawn with a syringe and immediately injected into a suspension of 400 mg of silica gel, previously activated at 580° C., in about 400 ml of dry, air-free hexane. The stock solution was then quickly cooled to −78° C. and maintained at this storage temperature. When brought into contact with ethylene at 75° to 100° C. and 300 psi, the supported allyl chromium oligomerized ethylene in a very exothermic reaction, to form butenes, hexenes, some higher hydrocarbon oils, and some traces of polymer of density 0.91 and melt index 6-50.

EXAMPLE 2

The stock solution prepared in Example 1 was then allowed to warm to room temperature (about 25° C.) and remain standing for about 20 minutes before a second 0.5 ml. sample was withdrawn and injected into a suspension of 400 mg. of silica gel, previously activated at 350° C., in about 100 ml. of dry air-free hexane. Deposition of the complex on the support was immediate and resulted in the formation of a red-brown sand. The stock solution was immediately returned to cold storage at −78° C. The catalyst sand was charged to a stirred auto-clave containing about 500 ml of dry air-free hexane held at about 50° C. The system was heated to 72°–75° C. and pressurized with ethylene to a pressure of 300 psi. Polymerization began immediately and more ethylene was fed on demand. After 35 minutes there was obtained 126 grams of a polymer having a Melt Flow of 0.1 dgm/min and a density of 0.957. The infrared spectrum of the ethylene polymer in the 10 to 11.3 micron region was found to differ from the infra-red spectra of so-called Ziegler resins. The productivity level of the catalyst was found to be greater than 6000 grams of polymer per gram of chromium per hour.

EXAMPLES 3-11

Using the stock solution prepared in Example 1 a series of polymerizations were carried out over a two week period using other supports, comonomers and modifying agents. In each instance the temperature of the stock solution was brought to 5° C. or more for removal of the catalyst sample and thereafter the stock solution was returned to cold storage. A maximum productivity level of greater than 400,000 grams of polymer per gram chromium per hour was obtained during this series of polymerization experiments.

As the solution aged (about Example 9) a reduction in activity was noticed and the amount of solution used in preparing the catalyst was increased reaching a maximum of 8 ml in later examples.

The results of this series of polymerization experiments are summarized in Table 1.

CONTROLS B AND C

Data derived from Examples 1 and 2 of U.S. Pat. No. 3,379,706 to Wilke are included for comparative purposes.

In Example 11 an ethylene-propylene copolymer was prepared. In the other Examples ethylene homopolymers were prepared.

The polymer produced in Example 3 had a density of 0.955. The polymer produced in Example 4 had a density of 0.945 and had a % methyl content of 0.24. The polymer produced in Example 5 had a density of 0.924 and a % methyl content of 1.14. The polymer produced in Example 10 had a density of 0.949 and a % methyl content of 0.16. The polymer produced in Example 11 had a density of 0.935. Butene-1 was formed as an oligomeric by-product in the reactions of Examples 4 through 10. No butene-1 was formed during the reaction of Example 3.

It appears that supported allyl chromium [II] is both an ethylene homopolymerization or ethylene α-olefin copolymerization catalyst, as well as an ethylene isomerization catalyst. Isomerization becomes relatively more important as the temperature of activation of the support is increased. When the support has been activated below 400° C., its use in the supported catalyst system leads to a polymerization reaction predominantly. When the support has been activated above 500° C., its use in the supported catalyst system leads to isomerization, which leads to oligomerization, becoming the more predominant reaction. The catalyst activation temperature range of 400°–500° C. represents a transition region with respect to the ability of the activated catalyst to cause a polymerization or isomerization reaction to occur. Supported allyl chromium [II] not only polymerizes ethylene to high molecular weight homopolymer, but also oligomerizes it to relatively low molecular weight olefins. Oligomerization also becomes relatively more important both as the support activation temperature and the reaction temperatures are increased. Supported allyl chromium [II] is an effective ethylene α-olefin copolymerization catalyst, giving rise to copolymers with densities in the medium density (0.94) range if the polymerization temperature is below about 100° C., and in the low density (0.91–0.92) if the solution (higher temperatures) process is used. Alternatively, "low density" polyethylene may be prepared in low yield by the particle form process if the support activation temperature is about 580° C. Ethylene/α-olefin copolymers of low density can be prepared if the support is activated at ≧400° C., see Example 15 below.

TABLE I

| | Catalyst | | | POLYMERIZATION DATA | | | | | | | | Polymer | |
|---|---|---|---|---|---|---|---|---|---|---|---|---|---|
| | | | | Polymerization Conditions | | | | | | | | Properties | |
| | Allyl Chromium | | | C$_2$H$_4$ | H$_2$ | C$_3$H$_6$ | C$_3$H$_6$ | Time | Yield | Productivity | | | |
| Example | m. moles | Support[1] | Temp °C. | psi | gr. | | % Polym. | Min. | Gr. | g/g Cr-Hr | | MI | MF |
| 3 | <0.7 | MSID-SiO$_2$ | 75–80 | 300 | 0 | — | — | 30 | 126 | 50,000 | | NF | 0.1 |
| 4 | <0.7 | " | 88–94 | 300 | 0 | — | — | 28 | 134 | 53,000 | | NF | 0.7 |
| 5 | <0.6 | " | 75–126 | 275 | 25 | — | — | 23 | 26 | — | | 0.6 | 91 |
| 6 | <0.2 | " | 86–90 | 270 | 30 | — | — | 36 | 86 | 400,000 | | 0.01 | 1.8 |
| 7 | <0.3 | ID-SiO$_2$ | 84–92 | 275 | 25 | — | — | 25 | 106 | >22,000 | | 0.02 | 2.4 |
| 8 | <0.6 | " | 86–90 | 250 | 50 | — | — | 20 | 62 | >6,000 | | 0.01 | 3.6 |
| 9 | >0.7 | MSID-SiO$_2$ | 83–94 | 300 | 0 | — | — | 20 | 92 | >7,600 | | NF | 1.0 |
| 10 | <1.4 | " | 90–94 | 200 | 100 | — | — | 30 | 133 | >3,700 | | 0.10 | 7.2 |
| 11 | <1.9 | ID-SiO$_2$ | 88–90 | 300 | 0 | 10 | 3.4 | 90 | 37 | >250 | | 0.03 | 7.1 |
| Control B | 3.4 | None | 20 | 738 | 0 | — | — | 300 | 5 | 5 | | — | NF |
| Control C | 3.4 | None | 43 | 735 | 0 | — | — | 300 | 32 | 36 | | — | — |

[1] Activated in Argon at 350° C.
NF = No Flow

EXAMPLES 12–16

Bis allyl chromium II was prepared by first reacting chromous chloride with allyl magnesium bromide at 25° C. under a slight argon pressure. Then the excess allyl magnesium bromide was destroyed with dry, oxygen free $CO_2$, and the bis allyl chromium II was recovered as disclosed in Example 1 above.

The thus produced bis allyl chromium II was then used to polymerize ethylene alone, or to copolymerize it with propylene, in a series of 5 polymerization reactions. The bis allyl chromium II compound was deposited on an activated silica support prior to the polymerization reactions from a hexane solution thereof so as to deposit about 0.3 millimoles of the chromium complex on about 400 milligrams of intermediate density silica. The silica had been previously activated at 340° or 400° C. The reactions were conducted as described in Example 2 above under a total pressure of 200 psig. In some cases about 70 psig of H$_2$ were used as part of the total 200 psig. The activation temperature of the support; the psig of H$_2$; the amount of propylene (in grams); and the polymerization times and temperatures used in these experiments are listed below in Table II. Also listed in Table II are the yields of polymer produced (in grams) in each of the experiments as well as the melt index (MI) and high load melt index (HLMI) properties of the resulting polymers. The relatively low melt index values for these polymers indicates that the polymers were solid materials of relatively high molecular weights.

1. A catalyst for the polymerization of ethylene which consists essentially of a π allyl chromium [III] complex wherein the ligands are only allyl ligands and at least a portion of the chromium is reduced to the chromium [II] valence state, said complex being supported on an inorganic oxide of high surface area and selected from the group consisting of silica and silica-alumina.

2. A catalyst as claimed in claim 1 in which substantially all of the π allyl chromium [III] complex is in the chromium [II] valence state.

3. A catalyst as in claim 2 in which the inorganic oxide support is silica.

4. A process for preparing an allyl chromium catalyst for the polymerization of ethylene which consists essentially of reducing at least a portion of the chromium in a π allyl chromium [III] complex wherein the ligands are only allyl groups to the chromium [II] valence state and depositing the reduced allyl chromium complex on an inorganic oxide of high surface area and selected from the group consisting of silica and silica-alumina.

5. A process as in claim 4 in which the inorganic oxide is silica.

6. A process as claimed in claim 4 in which the π allyl chromium [III] complex is reduced to the chromium [II] valence state at a temperature above −17° C.

7. A process as claimed in claim 6 in which substantially all of the π allyl chromium [III] complex is reduced to the chromium [II] valence state.

8. A process as claimed in claim 4 in which the allyl chromium complex is subjected to a temperature of between about −17° to about 80° C. for about 1 to

TABLE II

| | Support | | | Polymerization Yield | | | | |
|---|---|---|---|---|---|---|---|---|
| Example | Act. Temp. °C. | H$_2$ Psig. | C$_3$H$_6$ Grams | Temp. °C. | Time Min. | Grams | MI | HLMI |
| 12 | 340 | 0 | 0 | 88–91 | 40 | 130 | 0.01 | 1.6 |
| 13 | 340 | 70 | 0 | 89–90 | 30 | 30 | 0.02 | 2.2 |
| 14 | 340 | 70 | 0 | 88–90 | 90 | 86 | 0.03 | 5.0 |
| 15 | 400 | 0 | 13 | 87–93 | 165 | 122 | 2.7 | 143. |
| 16 | 400 | 0 | 0 | 120–130 | 150 | 70 | 24. | — |

The polymers produced in Examples 12, 15 and 16 had densities of 0.941, 0.920 and 0.910, respectively.

What is claimed is:

about 30 minutes prior to deposition onto the inorganic oxide support.

* * * * *